(12) United States Patent
Dinnean et al.

(10) Patent No.: US 8,528,747 B2
(45) Date of Patent: Sep. 10, 2013

(54) SOLID PHASE EXTRACTION DISK AND METHOD OF MANUFACTURE

(75) Inventors: Kevin Dinnean, Penacook, NH (US); Robert S. Johnson, Hampstead, NH (US); Steve J. MacDonald, Hudson, NH (US)

(73) Assignee: Horizon Technologies, Inc., Salem, NH (US)

( * ) Notice: Subject to any disclaimer, the term of this patent is extended or adjusted under 35 U.S.C. 154(b) by 548 days.

(21) Appl. No.: 12/703,514

(22) Filed: Feb. 10, 2010

(65) Prior Publication Data

US 2010/0200491 A1 Aug. 12, 2010

Related U.S. Application Data

(60) Provisional application No. 61/151,362, filed on Feb. 10, 2009.

(51) Int. Cl.
*B01D 24/00* (2006.01)
*B01D 37/02* (2006.01)

(52) U.S. Cl.
USPC ........... 210/503; 210/479; 210/484; 210/485; 210/496; 210/497.01; 210/500.26; 210/502.1; 210/504; 210/506

(58) Field of Classification Search
USPC .................... 210/479, 484, 485, 496, 497.01, 210/500.26, 502.1, 504, 506, 503
See application file for complete search history.

(56) References Cited

U.S. PATENT DOCUMENTS

| | | | |
|---|---|---|---|
| 4,753,776 A | 6/1988 | Hillman et al. | |
| 5,271,118 A | 12/1993 | Piotrowitz | |
| 5,538,634 A | 7/1996 | Pfiffner et al. | |
| 5,595,649 A | 1/1997 | Markell et al. | |
| 6,124,012 A * | 9/2000 | Jones et al. | 428/64.1 |
| 6,492,183 B1 | 12/2002 | Perman et al. | |
| 2006/0247362 A1 | 11/2006 | Shah | |

OTHER PUBLICATIONS

International Search Report dated Apr. 1, 2010 issued in related International Patent Application No. PCT/US10/23754.
Lifshutz, "On the 'Mean Flow' Pore Size Distribution of Microfiber and Nanofiber Webs," International Nonwovens Journal, vol. 14, No. 1, Spring 2005, pp. 18-24.

* cited by examiner

*Primary Examiner* — Krishnan S Menon
*Assistant Examiner* — Allison M Gionta
(74) *Attorney, Agent, or Firm* — Grossman, Tucker, Perreault & Pfleger, PLLC

(57) ABSTRACT

Solid phase extraction (SPE) disks may be manufactured by providing a suspension comprising glass microfibers and a suspension comprising one or more sorbents and forming a disk by combining the suspensions or by layering the suspensions. This may be followed by a drying procedure to create the finished disk. A disk mold including a collar and plug may be used to establish the size and shape of the disk. Examples of various constructions and processes for forming the disks are provided.

17 Claims, 3 Drawing Sheets

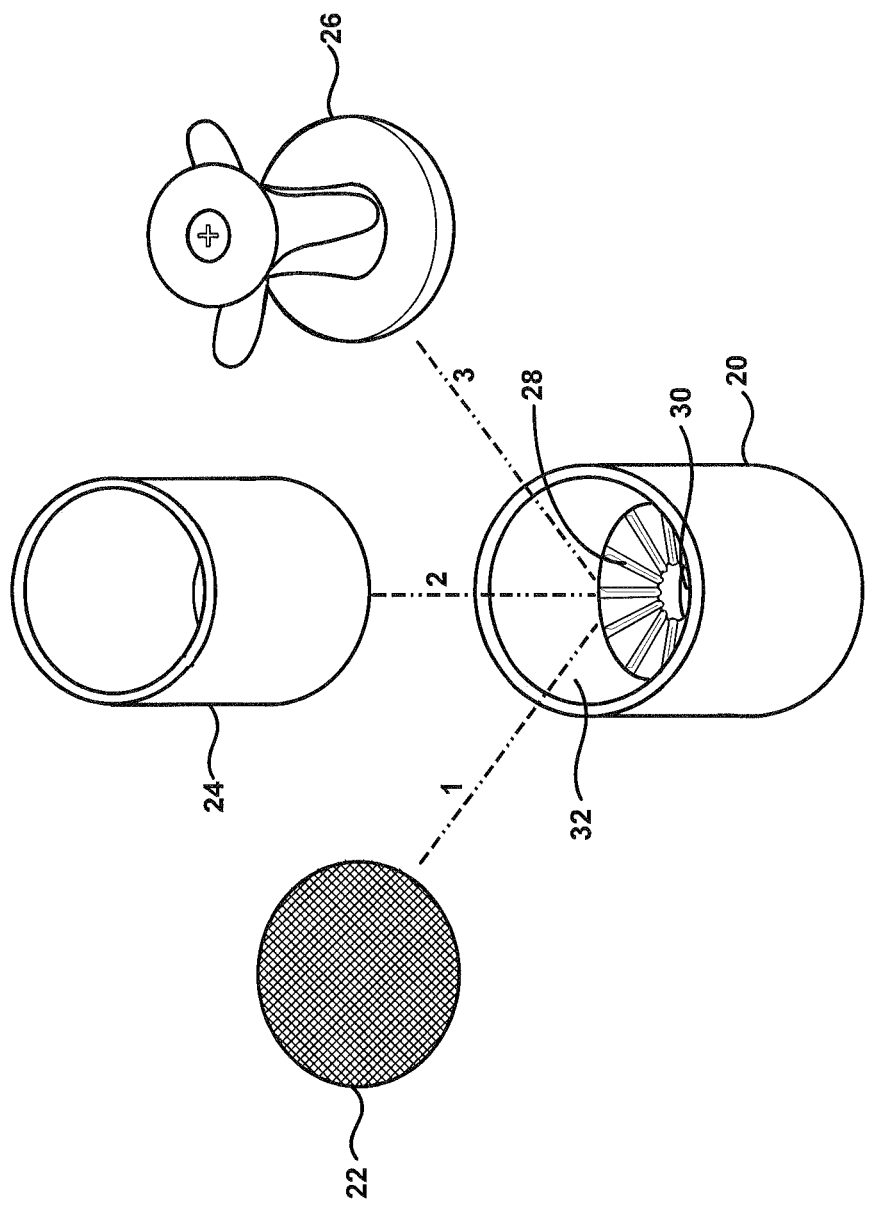

SOLID PHASE EXTRACTION DISK AND METHOD OF MANUFACTURE

CROSS REFERENCE TO RELATED APPLICATIONS

This application claims priority to U.S. provisional application Ser. No. 61/151,362, filed Feb. 10, 2009, which is incorporated by reference herein to the extent it is consistent.

FIELD

This invention relates generally to sample testing products and techniques, and more particularly to improved solid phase extraction (SPE) filtration disks and methods for their manufacture.

BACKGROUND

In the art which can be broadly described as separation science, means are provided for isolating, separating, and analyzing mixtures of solutions by selective adsorption on materials such as polymeric materials (e.g. polydivinylbenzene (PDVB) and polymer gel), alumina, silica, and bonded silica. The process is based on differences in the distribution ratios of the components of mixtures between a mutually immiscible mobile and a fixed stationary phase.

Solid phase extraction (SPE) is a laboratory technique for analyzing liquid and mixed liquid/solid samples. The basic objective of such apparatus is to filter the solid portion of the sample and to selectively adsorb compounds from the liquid portion onto a sorbent. The analytes of interest can be subsequently extracted with the solvent and eluted from the sorbent with a minimal amount of an appropriate solvent.

Typical SPE disk apparatus may dispose a sorbent-impregnated SPE disk between an upper funnel and a lower base. A sample may be poured into the funnel, and a vacuum source applied to the base to draw the sample through the disk. The process may be continued until all of the sample to be filtered has passed through the disk.

The analytes bound by the sorbents and trapped in solids filtered out by the disk may be collected by elution. The vacuum may be disconnected and a small amount of extraction solvent applied. The procedure may include a soak period, where analytes bound by the sorbents within the disk desorb and partition into the extraction solvent. After soaking, vacuum may be reapplied, and the solvent collected.

SUMMARY

A solid phase extraction (SPE) filtration disk comprises a cake, having glass microfibers and one or more sorbents, with a fiber mesh, which provides support and an outer covering on at least one side of the cake. In an exemplary embodiment, a layer of glass microfibers may be provided on one or more sides of the cake to increase the integrity of the disk, with the layer of glass microfibers in layered and/or in adjacent disposition with the cake. The sorbent may include polymeric materials, such as polystyrene-divinylbenzene (PS-DVB), and/or bonded silica materials including, but not limited to, carbon-18 bound silica, carbon-8 bound silica, tertiary amine bound silica and combinations thereof. Additional sorbent materials are also disclosed herein.

In an exemplary embodiment, a solid phase extraction filtration disk is provided which comprises an inner member located within an outer member. The inner member is in the form of a circular cake comprising a sorbent mixed with glass microfibers, with the cake having a first circular side, a cylindrical side and a second circular side. The outer member comprises a first circular portion covering the first circular side of the cake, a cylindrical ring portion covering the cylindrical side of the cake, and a second circular portion covering the second circular side of the cake. The outer member first circular portion comprises a microfiber mesh, while the outer member cylindrical ring portion and second circular portion comprise a layer of glass microfibers molded over the cylindrical side of the cake. The microfiber mesh may be a particulate filter media. The microfiber mesh may comprise a glass microfiber mesh, and the glass microfiber mesh may be a binderless borosilicate glass microfiber.

The outer member first circular portion may be joined directly with the first circular side of the cake.

The outer member cylindrical ring portion and outer member second circular portion may each comprise glass microfibers having a diameter in a range of 0.2-10 microns. The outer member cylindrical ring portion and outer member second circular portion may be of a same composition, which may be from a liquid suspension. The outer member cylindrical ring portion and the outer member second circular portion may comprise glass microfibers having a diameter in a range of 0.2-10 microns.

The outer member cylindrical ring portion may be of a first composition, and the outer member second circular portion may be of a second composition. The first composition may have a greater density than the second composition. The first composition may be from a first liquid suspension, and the second composition may be from a second liquid suspension.

The outer member cylindrical ring portion and outer member second circular portion may be molded in situ to the cylindrical side of the cake and the second circular side of the cake, respectively.

The sorbent may comprises at least one of a polymeric material or a bonded silica material.

In method form, solid phase extraction (SPE) disks may be manufactured by providing a suspension comprising glass microfibers and a suspension comprising one or more sorbents, mixing the suspensions, introducing the mixture of suspensions to a molding apparatus and thereafter evacuating the liquid phase of the suspensions from the molding apparatus, particularly with the aid of a vacuum. This may be followed by applying a suspension comprising glass microfibers over the cake and evacuating the liquid phase, particularly with the aid of a vacuum. This may be followed by a drying procedure to create the finished disk. A molding apparatus including a mold base, a collar and plug may be used to establish the size and shape of the cake, as well as the disk. A fiber mesh, such as a glass fiber mesh, may be used as a foundation for the sorbent/fiber cake. Examples of various constructions and processes for forming the disks are provided.

In one exemplary embodiment, a method of providing a solid phase extraction filtration disk comprises providing a molding apparatus having a cavity, placing a microfiber mesh in the cavity of the molding apparatus, introducing a mixture of sorbent and glass microfibers to the cavity over the microfiber mesh, molding the sorbent and glass microfibers to form a cake having an exposed cylindrical side and an exposed circular side, and forming a layer of glass microfibers over the exposed cylindrical side of the cake and exposed circular side of the cake, and molding a layer of glass microfibers over the exposed cylindrical side of the cake and exposed circular side of the cake.

Molding the layer of glass microfibers over the exposed cylindrical side of the cake and exposed circular side of the cake may be performed by applying a liquid suspension comprising glass microfibers over the exposed cylindrical side of the cake and exposed circular side of the cake and evaluating the liquid.

Molding the layer of glass microfibers over the exposed cylindrical side of the cake and exposed circular side of the cake may be performed by applying a first liquid suspension comprising glass microfibers over the exposed cylindrical side of the cake and then applying a second liquid suspension comprising glass microfibers over the exposed circular side of the cake and evaluating the liquid.

The molding apparatus may include a porous member; and the step of placing a microfiber mesh in the cavity of the molding apparatus may further comprise placing the microfiber mesh in the cavity of the molding apparatus over the porous member.

BRIEF DESCRIPTION OF THE DRAWINGS

The objects, features and advantages of the present invention will be apparent in the following detailed description thereof when read in conjunction with the appended drawings wherein the same reference numerals denote the same or similar parts throughout the several views.

FIG. 5 is an exploded view of the molding apparatus used in the present invention.

DETAILED DESCRIPTION

Figure 1:
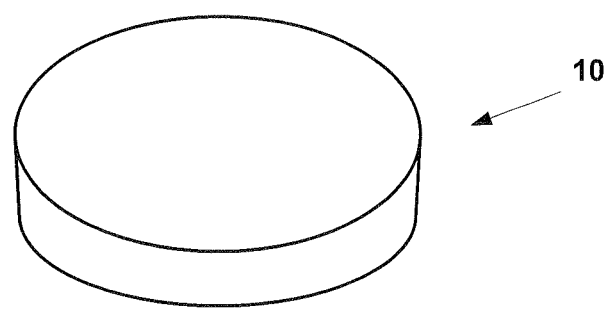
FIG. 1 is a perspective view of an exemplary SPE disk in accordance with the present invention.

Referring to the drawings, FIG. 1 is a perspective view of a solid phase extraction (SPE) filtration disk 10 according to the present disclosure. Generally, these disks 10 may be about 47 mm (millimeters) in diameter and in a range of and any increments between about 2-25 mm in thickness, although they may have other dimensions, e.g. diameters in a range of and any increments between 5-100 mm in diameter, and thickness in a range of and any increments between 1-50 mm in thickness.

The disk 10 may comprise an arrangement of various combinations of an inner member, particularly in the form of a circular cake 14, which may particularly comprise a mixture of sorbent and glass microfibers, in layered and/or in adjacent disposition with an outer member which particularly provides a covering for cake 14, which may particularly comprise glass microfibers.

Figure 2:
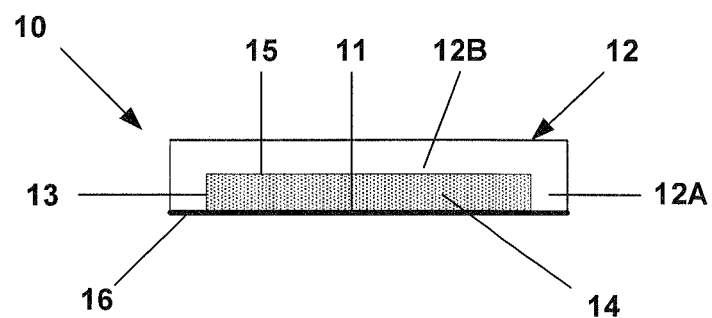
FIG. 2 is a cross-sectional view of the SPE disk of FIG. 1.

FIG. 2 is a cross-sectional view of the filtration disk 10 illustrating an exemplary configuration comprising a sorbent and glass microfiber cake 14 in which the sorbent and glass microfiber are dispersed as a mixture throughout the cake 14. Cake 14 is supported on and located in layered disposition within and between adjacent outer member portions 12 and 16, respectively, which together surround and encapsulate cake 14.

More particularly, a lower circular side 11 of cake 14 is covered by and located on an underlying outer member circular portion 16, which provides a foundation to support the use of cake 14 and disk 10. As further shown in FIG. 2, the remaining cylindrical side 13 of cake 14 and upper circular side 15 of cake 14 are covered and surrounded by overlying outer member cylindrical ring portion 12A and outer member circular portion 12B, respectively, of outer member 12. The outer member portions 12 and 16 may provide integrity to the sorbent/glass microfiber cake 14 so that it may be handled and used for the filtration purposes.

With respect to materials for cake 14, exemplary sorbent materials include polymeric materials, such as polydivinylbenzene (PDVB) and polystyrene-divinylbenzene (PS-DVB), and/or bonded silica materials including, but not limited to, carbon-18 bound silica, carbon-8 bound silica, tertiary amine bound silica and combinations thereof. Other sorbent materials may include molecularly imprinted polymer (MIP), sulfonated resins for strong cation exchangers, carboxylated moieties for weak cation exchangers (resin based), quaternary amines bound to either silica or resin for strong anion exchangers, and covalently bonded ligands for chelation or molecular recognition media (silica or resin based). The sorbent for cake 14 may have a weight percentage in a range of and any increments between 10-90 percent of the cake 14, and more particularly have a weight percentage in a range of and any increments between 25-75 percent of the cake 14, and even more particularly have a weight percentage in a range of and any increments between 40-60 percent of the cake 14, Exemplary glass microfibers for cake 14 may include product number 704BBC from Evanite Fiber Corp. Evanite 704BBC is an extremely pure glass wool. The glass microfibers are not surface treated, so they contain no additives that can absorb moisture or cause the microfibers to adhere to themselves. The glass microfibers disperse easily in water and other liquids with minimum energy (e.g. stay suspended in a water alcohol solution). The glass microfibers may have a length in a range of and any increments between 1 µm (microns or micrometers) to 3 mm, and more particularly have a length in a range of and any increments between 50 µm to 2 mm, and even more particularly have a length in a range of and any increments between 100 µm to 1 mm. The glass microfibers may have a diameter in a range of and any increments between 0.2-10 µm, and more particularly have a diameter in a range of and any increments between 0.3-8.5 µm. Even more particularly, the glass microfibers may have a diameter in a range of and any increments between 0.4-0.6 µm, such as 0.5 µm. The glass microfibers for cake 14 may also possess the ability to keep the sorbent suspended in a liquid slurry solution prior to being introduced to a mold as described in greater detail below. The glass microfiber for cake 14 may have a weight percentage in a range of and any increments between 10-90 percent of the cake 14, and more particularly have a weight percentage in a range of and any increments between 25-75 percent of the cake 14, and even more particularly have a weight percentage in a range of and any increments between 40-60 percent of the cake 14.

For the materials of outer member portion 12, outer member portion 12 also may particularly comprise the glass microfibers used for cake 14, and particularly product number 704BBC from Evanite Fiber Corp with the material characteristics as described above.

For the materials for outer member portion 16, outer member portion 16 may particularly comprise a fiber mesh, and more particularly a nonwoven (random) matrix glass fiber mesh comprising microfibers which may be provided in the form of a thin, planar configuration (e.g. flat circular sheet). Exemplary glass microfibers for outer member portion 16 include grade A-E glass microfiber mesh from I.W. Tremont, which comprises binderless, 100% borosilicate glass microfiber. Such may particularly provide a particulate depth filter for disk 10 and as such may be referred to as a porous fibrous filter media or paper which functions by trapping particulate within the random matrix of fibers found within the thickness of the media. Grade A-E may be considered to have a fine porosity and fast flow rate, with a 1.0 μm size particle retention and a DOP efficiency of 99.98%. The efficiency rating of the filter is characteristic of the complex pore structure that develops as the fibers over-lap. Additional properties for grade A-E, as well as other possible grades within the scope of the invention, are as follows:

TABLE I

| Grade | Particle Retention (μm) | Filtration Speed (sec.) | Thickness (mm) | Basis Weight (g/m$^2$) |
|---|---|---|---|---|
| A | 1.6 | 12 | 0.30 | 55 |
| B | 1.0 | 30 | 0.65 | 140 |
| C | 1.2 | 25 | 0.28 | 50 |
| D | 2.7 | 5 | 0.60 | 120 |
| E | 1.3 | 12 | 0.35 | 70 |
| A-E | 1.0 | 15 | 0.33 | 60 |

While outer member portion 16 may be particularly provided in the form of a fiber mesh, the sorbent/glass microfiber cake 14 and glass microfiber outer member portion 12 may be particularly provided by compositions formed from suspensions of glass microfibers and of sorbents in vehicles, such as deionized water and alcohol, casting or otherwise introducing a quantity of such in a molding apparatus (e.g. disk mold) and evacuating or otherwise removing the liquid portion, particularly with the aid of a vacuum. This will be described in greater detail in the examples that follow. The filter 10 so formed may then be dried in an oven.

FIG. 5 is an exploded view of exemplary molding apparatus used to manufacture the solid phase extraction (SPE) disk 10 according to the present disclosure. A mold base 20 may be provided to act as a forming mold including a cylindrical cavity 32, an evacuation port 30 and aspiration grooves 28. Mold base 20 may further include a porous member 22, such as a circular metal screen, may be first placed in the cavity 32 of mold base 20 (as illustrated by reference numeral 1), over the aspiration grooves 28 to provide a foundation to support the manufacturing the cake 14, and inhibit the disk 10 from deforming into the aspiration grooves 28 during the manufacture thereof. Outer member portion 16, which may particularly comprise a circular fiber mesh of glass microfibers, and which is preformed relative to cake 14 (i.e. prior to the formation of cake 14), may then be placed in the cavity 32 of mold base 20 over the porous member 22. Unlike porous base 22, outer member portion 16 becomes a permanent part of disk 10 upon the manufacture of disk 10. Conversely, porous base 22 is reused for the manufacturing of additional disks 10 and as such is separated from the disk 10 after the disk 10 is removed from cavity 32 of mold base 20.

A cylindrical collar 24 having an outer diameter approximating the inner diameter of the mold base 20 may then be used to establish the outer cylindrical dimensions (e.g. diameter) of the cake 14 by placing the collar 24 inside the cavity 32 of mold base 20 (as illustrated by reference numeral 2).

To form cake 14, a liquid suspension comprising glass microfibers and sorbent may then be poured or otherwise introduced into the cavity 32 of mold base 20 (within the confines of collar 24) and applied onto outer member portion 16, and any liquid from the suspension evacuated through aspiration grooves 28 and the port 30, particularly by applying a vacuum thereto in which case the aspiration grooves 28 form part of a vacuum chamber. In this manner, the cake 14 is molded in situ relative to outer member portion 16 to join outer member portion 16 directly at the lower circular side 11 of cake 14 and adhere the outer member portion 16 and the cake 14 together.

Subsequent to the formation of cake 14, the collar 24 may be removed from cavity 32 of mold base 20. Collar 24 may be particularly removed while vacuum is still applied to cake 14 to inhibit cake 14 from being removed from mold base 20 with collar 24. Thereafter, a composition in the form of a liquid suspension comprising glass microfibers may be poured into the cavity 32 of mold base 20 and above and around the cake 14, and any liquid from the suspension evacuated through aspiration grooves 28 and the port 30, particularly by applying a vacuum thereto. In this manner, a cylindrical ring portion 12A and upper circular portion 12B of outer member portion 12 are molded over and in situ around cake 14 to join outer member portion 12 with the cylindrical side 13 and upper circular side 15 of cake 14, respectively, and adhere the outer member portion 12 and cake 14 directly together. Additionally, cylindrical ring portion 12A of outer member portion 12 is molded over and in situ to a perimeter ring of outer member portion 16 to join cylindrical ring portion 12A of outer member portion 12 with outer member portion 16 and adhere the cylindrical ring portion 12A of outer member portion 12 and outer member portion 16 directly together. Cylindrical ring portion 12A, in addition to increasing the structural integrity of disk 10, also inhibits the sorbent material of the cake 14 from fragmenting and being lost from the perimeter of disk 10.

After evacuation to remove substantially all of the liquids, a disk 10 may be formed, as shown in FIG. 2 with circular side 11 of sorbent/glass microfiber cake 14 covered by underlying outer member portion 16, and cylindrical side 13 and circular side 15 of cake 14 covered by cylindrical ring portion 12A and upper circular portion 12B, respectively, of outer member portion 12.

Figure 3:
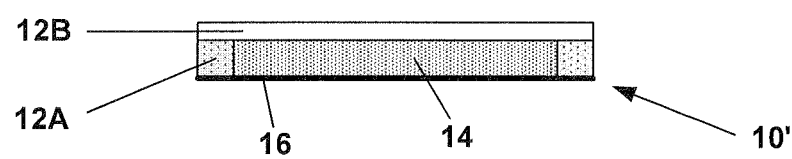
FIG. 3 is another exemplary cross-sectional view of an SPE disk.

In another embodiment, a plug 26, as shown in FIG. 5, may be placed on to the upper circular side 15 of cake 14 (as illustrated by reference numeral 3) and a different composition provided by a different liquid suspension comprising glass microfibers (other than the suspension for outer member portion 12B), as shown at 12A, may be poured or otherwise applied around the cylindrical periphery side 13 of the cake 14 and the liquid thereafter removed from the suspension through aspiration grooves 28 and the port 30, particularly by applying a vacuum thereto, to form cylindrical ring portion 12A of outer member portion 12 of the SPE disk 10' shown in FIG. 3. The plug 26 may then be removed and a composition provided by another liquid suspension comprising glass microfibers may be applied over circular surface 15 of cake 14 and cylindrical ring portion 12A of outer member portion 12, with the liquid thereafter removed from the suspension through aspiration grooves 28 and the port 30, particularly by applying a vacuum thereto, to form upper circular portion 12B of outer member 12. Thus, in this embodiment cylindrical ring portion 12A and upper circular portion 12B of outer member 12 are formed of different compositions from different liquid suspensions, whereas in the prior embodiment both were formed from the same composition. With the present embodiment, the percentage of glass microfibers and density in cylindrical ring portion 12A may be increased as compared to upper circular portion 12B to provide greater integrity to disk 10.

Figure 4:
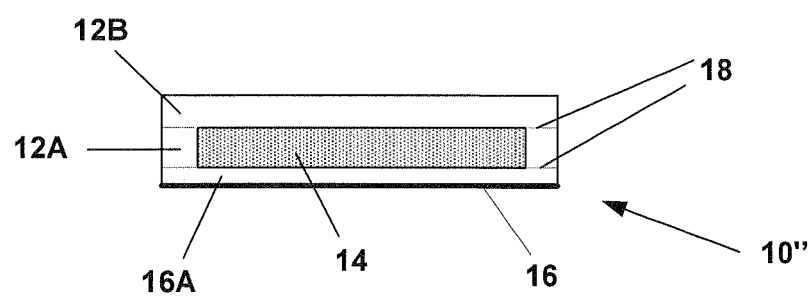
FIG. 4 is another exemplary cross-sectional view of an SPE disk.

In yet another embodiment, FIG. 4 illustrates in cross-section a disk 10" formed with a cake 14 of sorbent and glass microfibers surrounded by outer member portion 12 and 16A, which may particularly be provided from a liquid suspension comprising glass microfibers formed (molded) on both circular sides 11 and 13 of the cake 14 rather than just one side 13 as shown in the prior embodiments.

As described in Example E, the glass microfiber layers of circular outer member portion 16A may be formed by first pouring or otherwise introducing into the cavity 32 of mold base 20 a liquid suspension comprising glass microfibers applied onto outer member portion 16 and evacuating the liquid phase through aspiration grooves 28 and the port 30, particularly by applying a vacuum thereto. In this manner, outer member portion 16A is formed in situ on circular outer member portion 16 to join and adhere the outer member portion 16 and 16A together. Thus, in this embodiment, the outer member portion 16, 16A beneath subsequently formed cake 14 will comprise two layers. This may be followed by inserting the collar 24 in the cavity 32 of mold base 20 to form a cylindrical periphery for the cake 14.

Next, a liquid suspension comprising a sorbent and glass microfibers may be applied inside the collar 24 and any liquid evacuated through aspiration grooves 28 and the port 30, particularly by applying a vacuum thereto, to form cake 14. In this manner, the cake 14 is formed in situ relative to outer member portion 16A beneath it to directly join the outer member portion 16A at the lower circular side 11 of cake 14 and adhere the outer member portion 16A and the cake 14 together.

Thereafter, collar 24 may be particularly removed while vacuum is still applied to cake 14 to inhibit cake 14 from being removed from mold base 20 with collar 24. After removing the collar 24 from cavity 32 of mold base 20, a layer of glass microfibers for cylindrical ring portion 12A and upper circular portion 12B of outer member portion 12 may be formed by applying additional liquid suspension comprising glass microfibers above and around cake 14 and evacuating the liquid phase from cavity 32 of mold base 20, particularly by applying a vacuum thereto.

Alternatively, the plug 26 may be placed on the upper circular side 15 of cake 14 after the collar 24 has been removed and a second liquid suspension comprising glass microfibers, which may have a different length and/or diameter than the glass microfibers for used for outer member portion 16A, to form outer member cylindrical ring portion 12A around the cylindrical periphery side 13 around the cake 14. Subsequently, an additional layer of glass microfibers for upper circular portion 12B of outer member portion 12 may be formed over the cake 14, which may comprise the same composition used for outer member portion 16A The edges of the layers of glass microfibers are indicated by the dashed lines 18.

Example A

In a first example, liquid suspension comprising glass microfibers (S1) may be provided by adding about 11,356 mL (milliliter) of deionized water to a 19,000 mL container, followed by 51 grams of glass microfibers, such as 704BBC from Evanite Fiber Corp., and about 10 mL of concentrated HCl. These ingredients may be mixed using a Cuisinart and a Stir-Pak mixer for about 5 minutes on high speed to provide a relatively uniform dispersion and, in certain embodiments, to provide a microfiber length which may be less than the length of the microfibers prior to mixing.

A liquid suspension comprising sorbent (S2) may be provided by adding 400 mL of isopropanol to a 1,000 mL beaker followed by 16 grams of a polymeric sorbent such as C18 polydivinylbenzene from Jordi Polymeric (p/n 40512MS) and stirring the mixture with a spatula until the sorbent is relatively uniformly dispersed. Next, the 416 mL of S2 may be combined with 3,500 mL of Si and mixed thoroughly to form a glass/sorbent dispersion (S3).

Outer member portion 16 in the form of a 50 cm A-E glass microfiber mesh may be placed in a cavity 32 of mold base 20 (see FIG. 5) and a collar 24 inserted to establish the area of the sorbent cake 14 to be formed. Type A-E glass microfiber mesh 16 has a 50 cm diameter and a thickness of 0.3 mm, and may comprise binderless borosilicate glass microfiber with a 1.0 µm (micron) particle size retention, such as from I.W. Tremont.

Twenty-five (25) mL of suspension S3 may then be poured into in the cavity 32 of mold base 20 (within the confines of collar 24), overlying porous member 22, and the cavity 32 and a vacuum applied via outlet 30 until the liquid portion is substantially removed and a cake 14 is formed on the glass microfiber mesh 16. Note that the mold base 20 may include aspiration channels 28 to aid in evacuation of the liquid portion of the suspension and better ensure an even distribution or layer of glass microfibers and sorbent forms over fiber mesh 16. The collar 24 may then be then removed. Collar 24 may be particularly removed while vacuum is still applied to cake 14 to inhibit cake 14 from being removed from mold base 20 with collar 24. With the vacuum on, the cavity 32 of mold base 20 may next be filled with suspension S1 (about 100 mL) and a glass layer outer member 12 comprising cylindrical ring portion 12A and upper circular portion 12B drawn down onto and around the cake 14 of sorbent/glass. The resultant disk 10 may then be dried in an oven for about 12 hours at about 60° C. This disk construction is illustrated in FIG. 2.

Example B

In a second example, the same procedure as in Example A may be used to form a disk 10, except that a sorbent suspension (S4) may be formed by stirring 400 mL of isopropanol, 11.2 grams of C18 polymeric sorbent from Jordi Polymeric (p/n 40512MS) and 80 grams of C18 bound silica sorbent such as octadecylsilyl from Alltech (p/n 211503) with a spatula. To this sorbent suspension (S4), 3,500 mL of S1 glass microfiber suspension may be added and stirred thoroughly to form sorbent/glass microfiber suspension S5. About 25 mL of S5 may be poured into the cavity 32 of mold base 20 including glass microfiber mesh 16, porous member 22 and collar 24 and evacuated to form a cake 14, particularly be applying a vacuum thereto. After removing the collar 24 and with the vacuum on, the cavity 32 of mold base 20 may next be filled with suspension S1 (about 100 mL) and a glass layer for outer member 12 comprising cylindrical ring portion 12A and upper circular portion 12B drawn down on to and around the cake 14 of sorbent/glass. The resultant disk 10 may then be dried in an oven for about 12 hours at about 60° C.

Example C

In another example, to 11,356 mL of deionized water of deionized water, 51 grams of 704BBC glass microfibers and 10 mL of HCl (to bring the pH of the water to 2) may be added and mixed with a Magic Wand mixer on high speed for about 2 minutes.

In certain instances, due to the volume of liquid, better mixing may be achieved by mixing a fractional portion of the foregoing quantities, and thereafter combining the fractional mixed portions to form the entire batch (e.g. 3 portions of ⅓ each). The suspension (S6) may be allowed to stand for about 5 minutes, to allow the mixing device to cool, and then be mixed again for about 2 minutes to provide a relatively even dispersion.

Next, a sorbent suspension (S7) may be prepared by gently suspending 64 grams of polydivinylbenzene (PDVB) sorbent into 500 mL of methanol and stifling on a stir plate. After the suspension appears to be uniform, the total volume may be brought up to 800 mL. To about 3 liters of S6, 400 mL of S7 may be gently added and folded in using a spatula. The total volume may then be brought up to 4.4 liters by adding more of S6 and gently stirring with a spatula to form a DVB/microfiber suspension (S8).

One or more mold bases 20 may be provided. Type A-E glass microfiber mesh 16 may be added to each mold and wetted using deionized water. About 60 mL of suspension S6 may be added to the disk mold and quickly evacuated with a vacuum at about −20 inches of Hg (mercury) to form a glass microfiber layer.

Next, 50 mL of S8 may be added on top of the S6 glass microfiber layer and evacuated with a vacuum for approximately 1 minute. The disk may then be removed and dried in an oven for about 12-24 hours at 70° C.

Example D

In another example, a suspension (S1) may be provided by adding 11,356 mL of deionized water to a 19,000 mL container, followed by 51 grams of 704 BBC glass microfibers and 10 mL of concentrated HCl. These ingredients may be mixed using Cuisinart and Stir-Pak mixers for about 5 minutes on high speed.

Next, a glass microfiber suspension (S9) may be prepared by adding 11,356 mL of deionized water to a 19000 mL container, followed by 51 grams of 7804BBC glass microfibers and 10 mL of concentrated HCl. These ingredients may be mixed using a Cuisinart and a Stir-Pak mixer for about 6 minutes on high speed to provide a glass microfiber suspension S9 having a shorter fiber length than S1. This suspension may be used around the cylindrical ring portion of the cake layer (see reference numeral 12A in FIG. 3) to increase the density thereof.

This may be followed by the preparation of a sorbent suspension (S10) comprising 400 mL of methanol and 75 grams of Oasis polymeric sorbent (p/n WAT094287). The mixture may be stirred using a spatula and then combined with 3,500 mL of S1 to form sorbent/glass microfiber suspension S11.

A 50 cm A-E glass microfiber mesh 16 may be placed in the cavity 32 of mold base 20, overlying porous member 22, and the cavity 32 of mold base 20 filled to the rim (about 100 mL) with S1. The cavity 32 of mold base 20 may be evacuated, particularly with a vacuum, to draw the glass microfiber layer down (this forms 16A) and the collar 24 inserted and the vacuum turned off.

Fifty (50) mL of S11 may be added to the disk mold and vacuum applied to form a cake 14. The collar 24 may be removed and the vacuum turned off.

Next, a plug 26 may be inserted into the cavity 32 of mold base 20 centering it over the cake 14. The cylindrical ring space of cavity 32 between the plug 26 and mold base 20 may then be filled with S9 and vacuum applied to draw the glass microfiber layer down. With the vacuum on, the plug 26 may be removed and cavity 32 of the mold base 20 filled with S1 and vacuum applied until the glass microfiber layer is drawn down. The blunt end of the collar 24 may be applied to smooth out the disk edge. This may be followed by removing the disk 10 from the cavity 32 of mold base 20 and drying in an oven about 12 hours at 70° C. This construction is illustrated in FIG. 4.

Example E

In another example, a suspension (S1) may be provided by adding 11,356 mL of deionized water to a 19,000 mL container, followed by 51 grams of 704BBC and 10 mL of concentrated HCl. These ingredients may be mixed using Cuisinart and Stir-Pak mixers for about 5 minutes on high speed.

This may be followed by the preparation of a sorbent suspension (S12) comprising 800 mL of isopropanol and 160 grams of Oasis polymeric sorbent (p/n WAT094287). The mixture may be stirred using a spatula and then combined with 3,000 mL of S1 to form suspension S13.

A 50 cm A-E glass microfiber mesh 16 is placed in the cavity 32 of mold base 20, overlying porous member 22, and the cavity 32 of mold base 20 filled to the rim (about 100 mL) with S1. The mold base 20 may be evacuated to draw the glass microfiber layer down and the collar 24 inserted with the sharpened end down and the vacuum turned off.

Next, 25 mL of S13 may be added to the disk mold and evacuated to form a cake 14. The collar 24 may be removed and a plug 26 may be added, centered over the cake 14. The space, or cavity, between the plug 26 and the mold base 20 may next be filled with S1 and vacuum applied until the glass microfiber layer has been drawn down. With the vacuum on, the plug 26 may be removed and the mold base 20 filled with S1 and vacuum applied until the glass microfiber layer is drawn down. The blunt end of the collar 24 may be applied to smooth out the disk edge. This may be followed by removing the disk 10 from the mold base 20 and drying in an oven about 12 hours at 70° C. This construction is illustrated in FIG. 4.

It should be understood that, while the present invention has been described in detail herein, the invention can be embodied otherwise without departing from the principles thereof, and such other embodiments are meant to come within the scope of the present invention.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

What is claimed is:

1. A solid phase extraction filtration disk comprising:
   an inner member located within an outer member;
   the inner member in the form of a circular molded cake, the cake molded of a liquid suspension comprising a sorbent mixed with glass microfibers, wherein the sorbent and glass fibers are dispersed throughout the cake, the cake having a first circular side, a cylindrical side and a second circular side, and wherein the glass microfibers of the cake having a length in a range of 1 μm to 3 mm;
   the outer member comprising a first circular portion covering the first circular side of the cake, a molded cylindrical ring portion covering the cylindrical side of the cake, and a molded second circular portion covering the second circular side of the cake;

the outer member first circular portion comprising a microfiber mesh;

the outer member molded cylindrical ring portion comprising glass microfibers molded over the cylindrical side of the cake, wherein the glass microfibers of the outer member molded cylindrical ring portion having a length in a range of 1 μm to 3 mm; and the outer member molded second circular portion comprising glass microfibers molded over the second circular side of the cake, wherein the glass microfibers of the outer member molded second circular portion having a length in a range of 1 μm to 3 mm.

2. The disk of claim 1 wherein:
the microfiber mesh is a particulate filter media having a 1 micron size particle retention.

3. The disk of claim 1 wherein:
the microfiber mesh comprises a glass microfiber mesh.

4. The disk of claim 3 wherein:
the glass microfiber mesh is a binderless borosilicate glass microfiber.

5. The disk of claim 1 wherein:
the outer member first circular portion is joined directly with the first circular side of the cake.

6. The disk of claim 1 wherein:
the outer member cylindrical ring portion and outer member second circular portion each comprise glass microfibers having a diameter in a range of 0.2-10 microns.

7. The disk of claim 1 wherein:
the outer member cylindrical ring portion and outer member second circular portion are of a same composition.

8. The disk of claim 7 wherein:
the composition is from a liquid suspension.

9. The disk of claim 1 wherein:
the outer member cylindrical ring portion comprises glass microfibers having a diameter in a range of 0.2-10 microns.

10. The disk of claim 1 wherein:
the outer member second circular portion comprise glass microfibers having a diameter in a range of 0.2-10 microns.

11. The disk of claim 1 wherein:
the outer member cylindrical ring portion is of a first composition; and
the outer member second circular portion is of a second composition.

12. The disk of claim 11 wherein:
the first composition has a greater density than the second composition.

13. The disk of claim 11 wherein:
the first composition is from a first liquid suspension.

14. The disk of claim 11 wherein:
the second composition is from a second liquid suspension.

15. The disk of claim 1 wherein:
the outer member cylindrical ring portion is molded in situ to the cylindrical side of the cake.

16. The disk of claim 1 wherein:
the outer member second circular portion is molded in situ to the second circular side of the cake.

17. The disk of claim 1 wherein:
the sorbent comprises at least one of a polymeric material or a bonded silica material.

* * * * *